United States Patent [19]

Camaggi et al.

[11] Patent Number: 5,149,359
[45] Date of Patent: Sep. 22, 1992

[54] DERIVATIVES FROM 3,4-DEHYDRO-PIPERIDIN-5-ONE EXHIBITING A HERBICIDAL ACTIVITY

[75] Inventors: Giovanni Camaggi, Novara; Giovanni Meazza, Saronno; Ciro Preziuso, Opera, all of Italy

[73] Assignee: Agrimont S.p.A., Milan, Italy

[21] Appl. No.: 482,720

[22] Filed: Feb. 21, 1990

[30] Foreign Application Priority Data

Feb. 21, 1989 [IT] Italy .............................. 19498 A/89

[51] Int. Cl.$^5$ .................... A01N 43/40; C07D 211/86
[52] U.S. Cl. ........................................ 71/94; 546/205; 546/206; 546/216; 546/221; 546/219; 546/220; 546/242; 546/291; 546/292; 546/294; 546/295; 546/296; 546/297; 546/298; 546/299; 546/300; 546/301; 546/302
[58] Field of Search ............... 546/219, 242, 288, 292, 546/294, 296, 297, 298, 300, 205, 206, 216, 221, 220, 291, 295, 299, 301, 302; 71/94

[56] References Cited

U.S. PATENT DOCUMENTS 4,387,230 6/1983 White et al. .......................... 546/296
4,636,510 1/1987 Schneider et al. ................... 514/302

FOREIGN PATENT DOCUMENTS 565461 6/1979 Japan .................................. 546/297
2205316 12/1988 United Kingdom .

OTHER PUBLICATIONS

Tamura et al., Chemical Abstracts, vol. 93, No. 114467h (1980).

*Primary Examiner*—Patricia L. Morris
*Assistant Examiner*—Lenora Miltenberger
*Attorney, Agent, or Firm*—Stevens, Davis, Miller & Mosher

[57] ABSTRACT

The present invention relates to derivatives of 3,4-dehydropiperidin-5-one having herbicidal activity. The derivatives have the formula

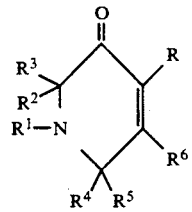

as defined in the claims. The present invention further relates to a herbicidal composition and a method for controlling weeds which grow among agricultural crops.

23 Claims, No Drawings

DERIVATIVES FROM 3,4-DEHYDRO-PIPERIDIN-5-ONE EXHIBITING A HERBICIDAL ACTIVITY

DESCRIPTION OF THE INVENTION

The present invention relates to derivatives of 3,4-dehydro-piperidin-5-one having herbicidal activity.

Therefore, an object of the present invention concerns compounds having general formula (I)

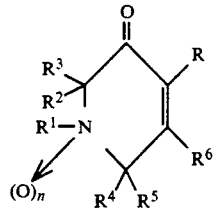

wherein:
R=—CO—R$^7$,

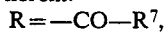

—NH—COR$^{10}$ (where R$^7$, R$^9$=C$_1$-C$_6$ alkyl, cycloalkyl, naphthyl, phenyl, phenyl substituted with halogens —CN, —NO$_2$, —CH$_3$, —SOCH$_3$, —OCH$_3$, CF$_3$; R$^8$=C$_1$-C$_6$ alkyl, C$_1$-C$_6$ alkyl containing 1-4 halogens, C$_2$-C$_6$ alkenyl, C$_2$-C$_6$ alkenyl containing 1-4 halogens, C$_3$-C$_6$ alkynyl, C$_3$-C$_7$ cycloalkyl, heterocycle with 5 or 6 atoms, C$_7$-C$_{20}$ aralkyl, phenyl, phenyl substituted with halogens, —CN, —NO$_2$, —CH$_3$, —O—CH$_3$, —CF$_3$; R$^{10}$=phenyl, phenyl substituted with halogens, —CN, —NO$_2$, —CH$_3$, —OCH$_3$, —CF$_3$);

R$^2$, R$^3$, R$^4$, R$^5$=like or unlike one another, are H, C$_1$-C$_3$ alkyl, C$_1$-C$_3$ alkyl substituted with 1-4 halogens; R$^6$=OR$^{11}$,

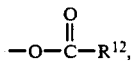

—S(O)$_m$—R$^{13}$, —NR$^{14}$R$^{15}$, halogen,

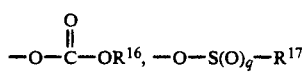

(where: R$^{11}$=H, alkaline or alkaline-earth metal; R$^{12}$, R$^{13}$ are C$_1$-C$_6$ alkyl optionally substituted with 1-11 halogens, C$_3$-C$_6$ cycloalkyl, C$_7$-C$_{20}$ aralkyl, phenyl, phenyl substituted with halogens, —CN, —NO$_2$, —CH$_3$, —OCH$_3$, —CF$_3$, dialkyl amino; m and q are 0, 1 or 2; R$^{14}$, R$^{15}$, like or unlike are H, C$_1$-C$_6$ alkyl, C$_1$-C$_6$ alkoxy; R$^{16}$=C$_1$-C$_6$ alkyl, C$_2$-C$_6$ alkenyl, C$_7$-C$_{20}$ aralkyl, phenyl, phenyl substituted with halogens, —NO$_2$, —CN, —CF$_3$, —CH$_3$, —OCH$_3$; R$^{17}$=C$_1$-C$_6$ alkyl, phenyl, phenyl substituted with halogens, —NO$_2$, —CN, —CF$_3$, —CH$_3$, —OCH$_3$);

R$^1$=phenyl, phenyl substituted with halogens, —NO$_2$, —CN, CF$_3$, alkyl, alkoxy, carbalkoxy, dialkylaminocarbonyl; C$_7$-C$_{20}$ aralkyl; C$_3$-C$_7$ cycloalkyl; the —OR$^{18}$ group (where R$^{18}$=C$_1$-C$_{10}$ alkyl; phenyl; phenyl substituted with halogens, alkyl, alkoxy, haloalkyl, —NO$_2$, —CN; aralkyl containing 7-20 carbon atoms, which is optionally substituted with 1-4 halogens); a

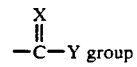

(where X=O or S, Y=phenyl; phenyl substituted with halogens, —NO$_2$, —CN, —CF$_3$, alkyl, alkoxy, aryloxy, arylamino; C$_3$-C$_6$ cycloalkyl; heterocycle with 5 or 6 atoms containing 1-4 hetero-atoms selected from the group comprising N, O, S; C$_1$-C$_8$ alkyl optionally substituted with 1-11 halogens; an —R$^{19}$—X$^1$—R$^{20}$ group, and —X—R$^{21}$ group; an —R$^{22}$—X$^1$—R$^{23}$—X$^2$—R$^{24}$ group; and —NR$^{25}$R$^{26}$ group, (wherein: R$^{19}$=C$_1$-C$_{16}$ alkyl, aralkyl; R$^{20}$=C$_1$-C$_{16}$ alkyl optionally substituted with 1-6 halogens, C$_3$-C$_6$ alkenyl, C$_3$-C$_6$ alkynyl, C$_3$-C$_7$ cycloalkyl, phenyl, substituted phenyl, C$_7$-C$_{13}$ phenylalkyl; R$^{21}$=C$_1$-C$_{16}$ alkyl optionally substituted with 1-6 halogens, C$_3$-C$_8$ alkenyl, C$_3$-C$_6$ alkynyl, C$_3$-C$_7$ cycloalkyl, aralkyl, aryl, substituted aryl, —R$^{19}$—X$^1$—R$^{20}$; R$^{22}$, R$^{23}$, R$^{24}$, like or unlike are C$_1$-C$_{16}$ alkyls; R$^{25}$, R$^{26}$, like or unlike are H, C$_1$-C$_{16}$ alkyl, C$_1$-C$_6$ alkoxy, phenyl optionally substituted with halogens, —NO$_2$, —CN, —CF$_3$, —OCF$_3$, alkyl, alkoxy, —SO$_2$—alkyl, —SO$_2$—aryl, —CO—aryl; X$^1$, X$^2$, like or unlike are O, S, SO, SO$_2$);

n=0, 1, on condition that when n=1, R$^1$=phenyl, substituted phenyl, C$_7$-C$_{20}$ aralkyl, C$_3$-C$_7$ cycloalkyl.

The aryl is preferably phenyl or naphthyl. Compounds having formula (I) are endowed with biological activity, in particular herbicidal activity. They are therefore fit to be used in agriculture in the defense of useful crops against weeds.

Compounds having formula (I) can be prepared by known reactions starting for instance, from a compound having formula (II). In particular, compounds having formula (I) where R$^6$=OH and R is

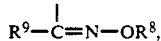

can be prepared according to the following reactions.

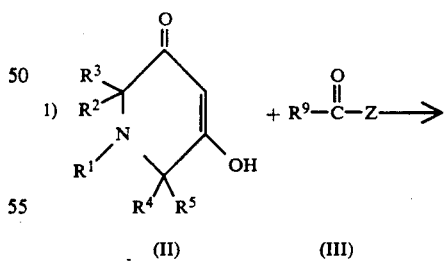

(II)  (III)

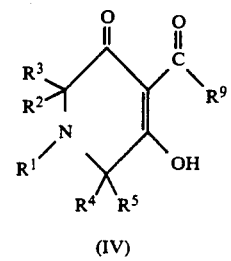

(IV)

-continued wherein Z = 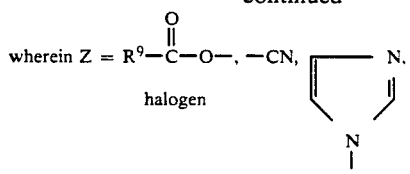

2) (IV) + H$_2$NOR$^8$ ⟶ 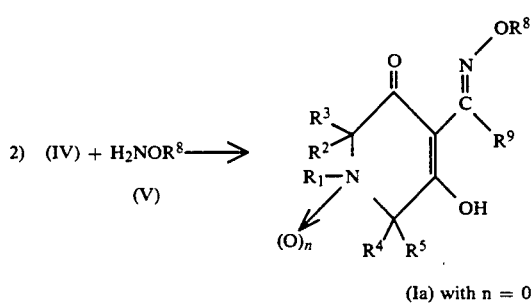

(Ia) with n = 0

3) (Ia) with n=0 oxidation (Ia) with n=1

According to reaction 1, intermediates (IV) are prepared by reacting compound (II) with an acylating agent having formula (III) in the presence of an organic or inorganic base, or optionally in the presence of bipolar aprotic solvents at temperatures from 0° C. to the boiling temperature of the reaction mixture.

The acylating agents which can be used are for example anhydrides of carboxylic acids, acyl halides, acyl-cyanides or an acyl-imidazole.

The base which can be used is for instance sodium hydride, potassium terbutylate, sodium methylate or sodium ethylate.

The solvents which can be used are for example dimethyl-formamide or dimethyl sulfoxide.

Compounds having formula (II) can in turn be prepared according to well known methods described, for instance, by Y. Tamura, L. C. Chen, M. Fujita and Y. Kita, J. Heterocyclic Chem., 17, 1(1980).

According to reaction 2, intermediates having formula (IV) are reacted with an oxamino compound of formula (V) in order to produce compounds having formula (Ia) where n=0, in a hydroalcoholic solvent, at temperatures from 0° C. to the boiling temperature of the reaction mixture, in accordance with a methodology, for example, as described in "Organic Functional Group Preparation" Vol. 3, 372–381 (1982), Academic Press-New York.

As for compounds of formula(V), it is possible to use the products of the deactivation of the corresponding hydrochlorides with a base, such as sodium hydroxide or potassium hydroxide and sodium acetate.

According to reaction 3, compounds having formula (Ia) where n=0 are oxidized to compounds having formula (Ia) where n=1, by using oxidizing agents, such as H$_2$O$_2$ or peracids, in inert organic solvents, such as CH$_2$Cl$_2$ or CHCl$_3$, at temperatures from 31 20° C. to room temperature.

As mentioned above, compounds having formula (I) exhibit interesting biological activities and, in particular, high herbicidal activity, which makes them suitable for use in agriculture in the defense of useful crops against weeds.

Their herbicidal activities appear on a wide variety of weeds. Furthermore, they bear a substantial compatibility or an absence of toxic effects on useful plants in pre- and post-emergence treatments.

In particular the herbicidal activity of compounds of formula (I) has turned out to be decidedly high regarding monocotyledons, and these compounds have shown no toxic effect on important agrarian crops like soya, beetroot and cotton.

As for their practical use in agriculture, the compounds of the present invention can be employed as such or, according to normal practice, in the form of an appropriate composition.

In addition to the compound of formula (I), as an active ingredient, inert carriers (which can be both liquid or solid) and if necessary other additives of agrarian use are also present in the compositions.

According to the normal practice adopted for formulations, compositions may appear in the form of liquid concentrates, emulsifiable concentrates, suspensions, powdered or wettable-powdered compounds and granular compounds.

If one wishes, in order to face specific situations, it is possible to add other active substance which are useful in agriculture such as fertilizers, fungicides or other herbicides to the compositions.

The amount of the compound of formula (I) to be used in the defense of useful crops against weeds depends on different factors. Among these, the following can be taken into consideration: the kind and degree of infestation, the type of treatment (whether pre- or post emergence), the relative effectiveness of the specific product of formula (I) also used in relation to the factors mentioned hereinbefore, the kind of crop on which the herbicide treatment is carried out, the formulation used and the climatic and environmental factors.

Generally satisfactory results are obtained by using a quantity of compound of formula (I) in the range of form 0.1 to 3 kg/ha.

The invention will now be illustrated by the following examples.

In the nuclear magnetic resonance spectrum at proton $^1$H-NMR), as shown in the hereinafter examples, the following abbreviations are used

| | |
|---|---|
| S = singlet | t = triplet |
| dd = doublet of doublets | q = quartet |
| d = doublet | m = multiplet |
| b = broad | |

EXAMPLE 1

Preparation of 1-(2-ethylthiopropanoyl)-4 -[1-(ethoximino)butyl] piperidin-3,5-dione. (compound No. 1)

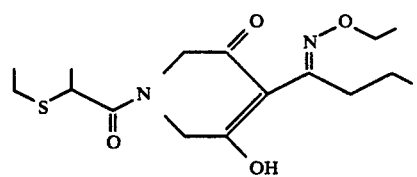

In a 50 ml two-necked flask, supplied with a cooler, thermometer and magnetic agitation, 1.5 g of 4-butanol-1-(2-ethylthiopropanoyl)piperidin-3,5-dione are introduced. The latter, which is prepared in the hereinafter example 3, is dissolved in 23 ml of water and 1.4 ml of methanol.

At room temperature, 0.49 g of ethoxyamine hydrochloride and 0.41 g of sodium acetate are then added.

The reaction mixture is heated at 50° C. for two hours while the solvent is left to evaporate. The reaction mixture is then diluted in water and extracted with dichloromethane.

The solvent is removed through reduced pressure distillation and the crude product undergoes a silica gel chromatography (dichloromethane eluant) in order to give 0.3 g of product in the form of a yellow oil.

¹H-NMR(CDCl₃): 0.95–1.72 (m, 14H, aliphatic); 2.53 (q, 2H, —CH₂S); 3.00

(t, 2H, —CH₂C=N—);
        |

3.62

(q, 1H, \CHS);
           /

4.10 (q, 2H, —CH₂O—); 4.3 (s, 4H, heterocyclic); 14.8 (bs, 1H, —OH).

EXAMPLE 2

Starting from the intermediates described in the hereinafter example 3 and operating under conditions similar to those described in example 1, the following compounds were prepared:

starting from 4-butanoyl-1-(3-methylbutanoyl)piperidin-3, 5-dione and ethoxyamine hydrochloride, the following was prepared: 4-[1-(-ethoximino)butyl]-1-(3-methylbutanoyl) piperidin-3,5-dione. (compound No. 2)

¹H-NMR(CDCl₃): 0.85–1.75 (m, 15H, aliphatic); 2.20

(d, 2H, —CH₂C=O)
          |

2.94

(t, 2H, —CH₂C=N—);
          |

3.73–4.26 (m, 6H, heterocyclic, —CH₂O—); 14.3 (bs, 1H, —OH). starting from 4-butanoyl-1-(3-methylbutanoyl)piperidin-3,5-dione and 3-chloroallyloxyamine hydrochloride, the following was prepared: 4-[1-(3-chloroallyloximino)butyl]-1(3-methylbutanoyl)-piperidin-3,5-dione. (compound No. 3)

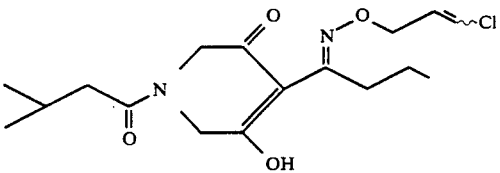

¹H-NMR(CDCl₃): 0.82–1.75 (m, 12H, aliphatic); 2.19

(d, 2H, —CH₂—C=O);
              |

2.93

(t, 2H, —CH₂—C=N—);
              |

4.19–4.28 (m, 4H, heterocyclic); 4.76 (d, 2H, —CH₂O—);
5.81–6.63 (m, 2H, —CH=CHCl); 14.3 (bs, 1H, —OH).

Starting from 4-butanoyl-1-(n-pentanoyl)piperidin-3,5-dione and ethoxyamine hydrochloride, the following was prepared: 4-[1-(ethoximino)butyl]-1-(n-pentanoyl) piperidin-3,5-dione. (compound No. 4)

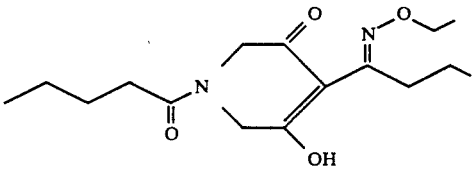

¹H-NMR(CDCl₃): 0.86–1.92 (m, 15H, aliphatic); 2.10–2.61

(m, 2H, —CH₂—C=O);
            |

2.97

(t, 2H, —CH₂—C=N—);
            |

3.84–4.30 (m, 6H, heterocyclic, —CH₂O—);
14.2 (bs, 1H, —OH).

Starting from 4-butanoyl-1-(2-ethylthiopropanoyl) piperidin-3,5-dione and cis-3-chloroallyloxyamine hydrochloride, the following was prepared: cis-4-[1-(3-chloroallyloximino)butyl]-1-(2-ethylthiopropanoyl) piperidin-3,5-dione. (compound No. 5)

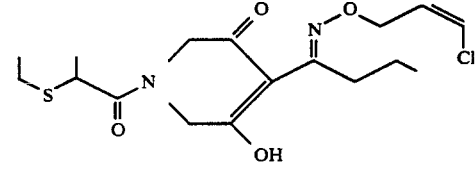

¹H-NMR(CDCl₃): 0.81–1.82 (m, 11H, aliphatic); 2.52 (q, 2H, —CH₂S—); 2.92

(t, 2H, —CH₂—C=N—);

3.61

(q, 1H, \CH—S—);

4.32 (s, 4H, heterocyclic); 4.75 (d, 2H, —CH₂O—); 5.80–6.40 (m, 2H, —CH=CHCl); 14.1 (bs, 1H, —OH).

Starting from 4-butanoyl-1-(2-ethylthiopropanoyl)piperidin-3,5-dione and trans-3-chloroallyloxyamine hydrochloride, the following was prepared: trans-4-[1-(3-chloroallyloximino)butyl]-1-(2-ethylthiopropanoyl)piperidin-3,5-dione. (compound No. 6).

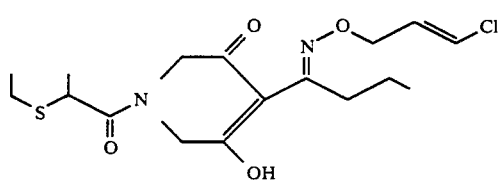

¹H-NMR(CDCl₃): 0.73–1.72 (m, 11H, aliphatic); 2.52 (q, 2H, —CH₂S—); 2.92

(t, 2H, —CH₂—C=N—);

4.32 (s, 4H, heterocyclic); 4.49 (d, 2H, —CH₂O—); 5.80–6.51 (m, 2H, —CH=CHCl); 14.1 (bs, 1H, —OH).

Starting from 4-butanoyl-1-(cyclohexanoyl)piperidin-3,5-dione and ethoxyamine hydrochloride, the following was prepared: 1-(cyclohexanoyl)-4-[1-(ethoximino)butyl] piperidin-3,5-dione. (compound No. 7).

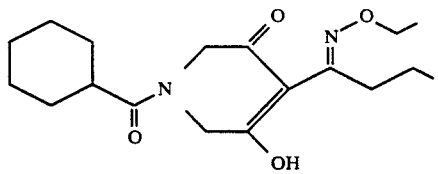

¹H-NMR(CDCl₃): 0.76–1.68 (m, 18H, aliphatic and cyclo-aliphatic); 2.41

(m, 1H, \CH—C=O—);

2.96

(t, 2H, —CH₂—C=N—);

4.10 (q, 2H, —CH₂O—); 4.22 (s, 4H, heterocyclic); 14.4 (bs, 1H, —OH).

Starting from 4-butanoyl-1-(ethoxycarbonyl)piperidin-3,5-dione and ethoxyamine hydrochloride, the following was prepared: 1-(ethoxycarbonyl)-4-[1-(ethoximino)butyl)] piperdin-3,5-dione. (compound No. 8)

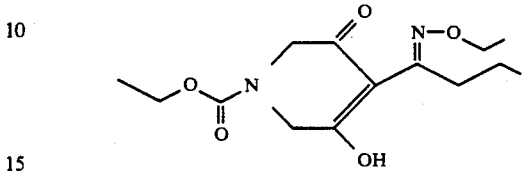

¹H-NMR(CDCl₃): 0.82–1.81 (m, 11H, aliphatic); 2.95 (t, 2H, —CH₂—C=N—); 3.92–4.30 (m, 8H, heterocyclic,

—CH₂—O—C=O,

—CH₂—O);

14.3 (bs, 1H, —OH).

Starting from 4-butanoyl-1-(2,4,6-trimethylbenzoyl)piperidin-3,5-dione and ethoxyamine hydrochloride, the following was prepared: 4-[1-(ethoximino)butyl]-1-(2,4,6-tri methylbenzoyl)piperidin-3,5-dione. (compound No. 9)

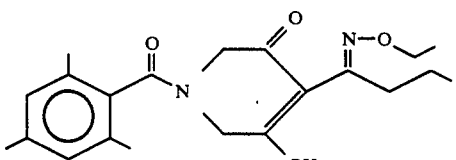

¹H-NMR(CDCl₃): 0.85–1.60 (m, 8H, aliphatic); 2.25 (s, 9H, CH₃ aromatic); 3.03

(t, 2H, —CH₂—C=N—);

3.90 (s, 2H, heterocyclic); 4.19 (q, 2H, —CH₂O); 4.62 (s, 2H, heterocyclic); 7.00 (s, 2H, aromatic); 14.42 (bs, 1H, —OH).

Starting from 4-butanoyl-1-(2,4-dichlorobenzoyl)piperidin-3,5-dione and ethoxyamine hydrochloride, the following was prepared: 1-(2,4-dichlorobenzoyl)-4-[1-(ethoximino)butyl] piperidin-3,5-dione. (compound No. 10)

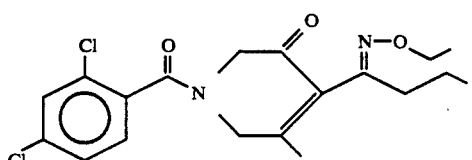

¹H-NMR(CDCl₃): 0.85–1.75 (m, 8H, aliphatic); 3.01

(t, 2H, —CH₂—C=N—);

3.93 (s, 2H, heterocyclic); 4.12 (q, 2H, —CH₂O—); 4.51 (s, 2H, heterocyclic); 7.30–7.44 (m, 3H, aromatic) 14.62 (bs, 1H, —OH).

Starting from 4-butanoyl-1-(2,4-dichlorobenzoyl) piperidin-3.5-dione and cis-3-chloroallyloxyamine hydrochloride, the following was prepared: cis-4-[1-(3-chloroallyloximino)butyl]-1-(2,4-dichlorobenzoyl)-piperidin-3,5-dione. (compound No. 11)

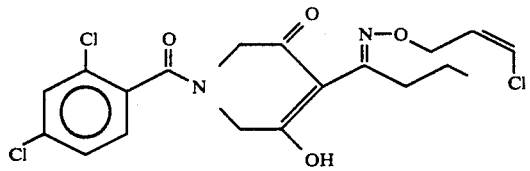

¹H-NMR)CDCl₃): 0.95 (t, 3H, CH₃); 1.48 (m, 2H, —CH₂—CH₃); 2.92

(t, 2H, —CH₂—C=N—);

3.88 (s, 2H, heterocyclic); 4.48 (s, 2H, heterocyclic); 4.71

(d, 2H, CH₂—C=C—);

5.78–6.39 (m, 2H, —CH=CHCl,); 7.22–7.39 (m, 3H, aromatic); 14.6 (bs, 1H, —OH).

Starting from 4-butanoyl-1-(2,4-dichlorobenzoyl)-piperidin-3,5-dione and trans-3-chloroallyloxyamine hydrochloride, the following was prepared: trans-4-[1-(3-chloroallyloximino)butyl] 1-(2,4-dichlorobenzoyl)-piperidin-3,5-dione. (compound No. 12)

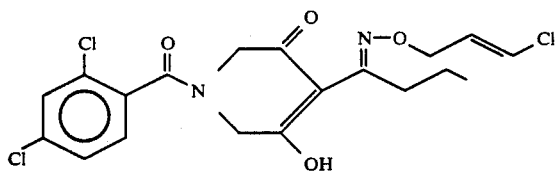

¹H-NMR(CDCl₃): 0.95 (t, 3H, CH₃); 1.54 (m, 2H, —CH₂—CH₃); 2.92

(t, 2H, —CH₂—C=N—);

3.91 (s, 2H, heterocyclic); 4.44–4.55 (m, 4H, heterocyclic,

—CH₂—C=C—);

5.85–6.54 (m, 2H, —CH=CHCl); 7.26–7.42 (m, 3H, aromatic) 14.5 (bs, 1H, —OH).

Starting from 4-propanoyl-1-(4-chlorobenzoyl)-piperidin-3,5-dione and ethoxyamine hydrochloride, the following was prepared: 1-(4-chlorobenzoyl)-4-[1-(ethoxyimino)propyl] piperidin-3,5-dione. (compound No. 13)

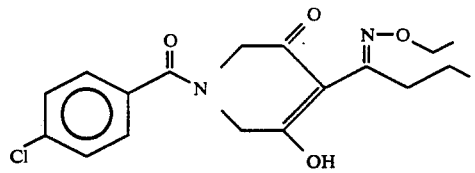

¹H-NMR(CDCl₃): 1.16 (t, 3H, CH₃); 1.35 (t, 3H, —CH₃); 3.02

(q, 2H, —CH₂—C=N—);

4.10 (q, 2H, q, 2H, CH₂O); 4.30 (s, 4H, heterocyclic); 7.37 (s, 4H, aromatic); 14.61 (bs, 1H, —OH).

Starting from 4-butanoyl-1-(2,6-dichlorobenzoyl)-piperidin-3,5-dione and ethoxymine hydrochloride, the following was prepared: 1-(2,6-dichlorobenzoyl)-4-[1-(ethoximino) butyl] piperidin-3,5-dione. (compound No. 14)

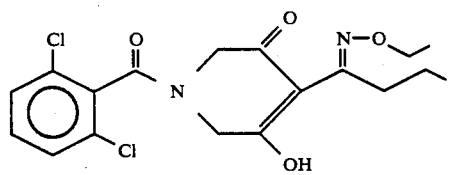

¹H-NMR(CDCl₃): 0.83–1.73 (m, 8H, aliphatic); 2.98

(t, 2H, —CH₂C=N—);

3.85 (s, 2H, heterocyclic); 4.18 (q, 2H, —CH₂O—); 4.51 (s, 2H, heterocyclic); 7.29 (s, 3H, aromatic); 14.10 (bs, 1H, —OH);

Starting from 4-propanoyl-1-(2,6-dichlorobenzoyl) piperidin-3,5-dione and ethoxyamine hydrochloride, the following was prepared: 1-(2,6-dichlorobenzoyl)-4-[1-(ethoximino)propyl] piperidin-3,5-dione. (compound No. 15)

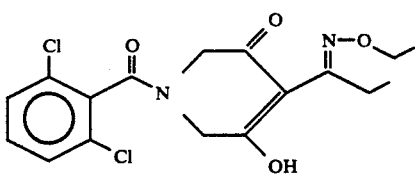

¹H-NMR(CDCl₃): 0.90–1.43 (m, 6H, aliphatic); 2.95

(t, 2H, —CH₂—C=N—);

3.89–4.29 (m, 4H, heterocyclic, —CH₂O);
4.52 (s, 2H, heterocyclic); 7.29 (s, 3h, aromatic); 14.12 (bs, 1H, —OH).

Starting from 4-butanoyl-1-(4-nitrobenzoyl)piperidin-3,5-dione and ethoxyamine hydrochloride, the following was prepared: 4-[1-(ethoximino)butyl]-1-(4-nitrobenzoyl) piperidin-3,5-dione. (compound No. 16)

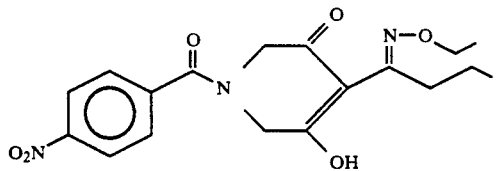

¹H-NMR(CDCl₃): 0.90–1.80 (m, 8H, aliphatic); 3.05

(t, 2H, —CH₂—C=N—);

4.01–4.38 (m, 6H, heterocyclic, —CH₂O); 7.15–8.41 (dd, 4H, aromatic); 14.02 (bs, 1H, —OH).

Starting from 4-butanoyl-1-(phenyl)piperidin-3,5-dione and ethoxyamine hydrochloride, the following was prepared: 4-[1-(ethoximino)butyl]-1-(phenyl)piperidin-3,5-dione. (compound No. 17)

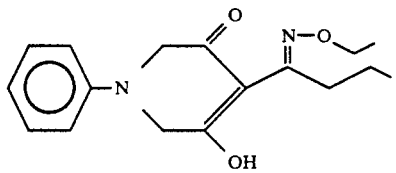

¹H-NMR(CDCl₃): 0.82–1.75 (m, 8H, aliphatic); 2.99

(t, 2H, —CH₂—C=N—);

3.98 (s, 4H, heterocyclic); 4.08 (q, 2H, —CH₂O—); 6.81–7.38 (m, 5H, aromatic); 15.10 (bs, 1H, —OH).

Starting from 4-propanoyl-1-(benzyl)piperidin-3,5-dione and ethoxyamine hydrochloride, the following was prepared: 1-(benzyl)-4-[1-(ethoximino)propyl] piperidin-3,5-dione. (compound No. 18)

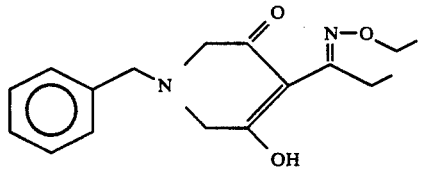

¹H-NMR(CDCl₃): 1.15 (t, 3H, CH₃) 1.28 (t, 3H, —CH₃) 2.98

(q, 2H, —CH₂—C=N—);

3.21 (s, 4H, heterocyclic); 3.56

(s, 2H, —CH₂—N<);

3.99 (q, 2H, —CH₂O); 7.29 (s, 5H, aromatic); 14.40 (bs, 1H, —OH).

Starting from 4-butanoyl-1-(N,N-dimethylamino carbonyl) piperidin-3,5-dione and ethoxyamine hydrochloride the following compound was prepared: 1-(N,N-dimethylaminocarbonyl)-4-[1-(ethoxyimino)butyl] piperidin-3,5-dione (compound No. 19)

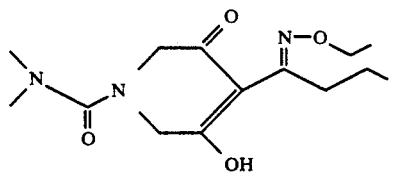

¹H-NMR(CDCl₃): 0.95 (t, 3H, CH₃); 1.2–1.8 (m, 5H, aliphatic); 2.8 (s, 6H, —N(CH₃)₂); 3.0

(t, 2H, —CH₂—C=N—);

3.9 (s, 4H, heterocyclic); 4.1 (q, 2H, —CH₂—O); 14.8 (bs, 1H, OH).

Starting from 4-butanoyl-1-(N,N-dimethylaminocarbonyl)-2-methyl-piperidin-3,5-dione and ethoxyamine hydrochloride the following compound was prepared: 1-(N,N-dimethylaminocarbonyl)-4-[1-(ethoxyimino)-butyl]-2-methyl-piperidin-3,5-dione (compound No. 20)

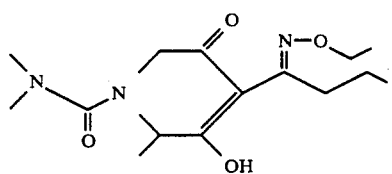

¹H-NMR(CDCl₃): 1.0 (t, 3H, CH₃); 1.3–1.9 (m, 8H, aliphatic); 2.8 (s, 6H, —N(CH₃)₂); 2.9

(t, 2H, —CH₂—C=N—);

3.7–4.5 (m, 5H, heterocyclic and —CH₂—O); 14.4 (s, 1H, OH).

EXAMPLE 3

Preparation of intermediate ketones.

In a 100 ml three-necked flask, which is supplied with a thermometer, cooler and a dropping funnel, 5.85 g of 1-(2-ethylthiopropanoyl)piperidin-3,5-dione dissolved in b 60 ml of anhydrous dimethylformamide are added under nitrogen.

The mixture is heated at 50°–60° C. and 1.22 g of sodium hydride at 50% are added in portions of oil.

When all the gas is evolved, 4.42 g of butyric anhydride are dripped and the remaining mixture is heated at 110° C. for 1½ hours.

The mixture is then diluted with water, extracted with ethyl acetate and dried with sodium sulphate. The solvent is then distilled at reduced pressure.

The crude product then undergoes a silica gel chromatography (eluant: chloroform/methanol 95:5). 1.5 g of 4-butanoyl-1-(2-ethylthiopropanoyl)piperidin-3,5-dione, having a melting point of 48°–50° C. is obtained:

$^1$H-NMR(CD$_3$OD): 0.70 –1.27 (m, 11H, aliphatic); 2.22 (t, 2H, —CH$_2$—S—); 2.55

(t, 2H, —CH$_2$—C=O);

3.61

(q, 1H, \\CH—S—/);

4.48 (s, 4H, heterocyclic); 17.9 (bs, 1H, —OH).

Operating under conditions similar to those described above and starting from 1-(3-methylbutanoyl)piperidin-3,5-dione and butanoic anhydride, the following compound was obtained: 4-butanoyl-1-(3-methylbutanoyl)-piperidin-3,5-dione.

$^1$H-NMR(CD$_3$OD): 0.89–1.72 (m, 12H, aliphatic); 2.20

(d, 2H, —CH$_2$CON/\\);

2.75

(t, 2H, —CH$_2$—C=O);

4.20 (s, 4H, heterocyclic); 18.0 (bs, 1H, —OH).

Starting from 1-(n-pentanoyl)piperidin-3,5 dione and butanoic anhydride, the following was prepared: 4-butanoyl-1-(n-pentanoyl)piperidin-3,5-dione.

$^1$H-NMR(CDCl$_3$): 0.89–1.78 (m, 12H, aliphatic); 2.29

(m, 4H, —CH$_2$—C=O, CH$_2$CON/\\);

4.12 (s, 4H, heterocyclic); 18.0 (bs, 1H, —OH).

Starting from 1-(cyclohexanoyl)piperdine-3,5-dione and butanoic anhydride, the following was prepared: 4-butanoyl-1-(cyclohexanoyl)piperidin-3,5-dione.

$^1$H-NMR(CDCl$_3$): 0.77–1.99 (m, 15H, aliphatic, cycloaliphatic); 2.62

(m, 1H, \\CH—C=O/);

2.90

(t, 2H, —CH$_2$—C=O);

4.25 (s, 4H, heterocyclic); 18.2 (bs, 1H, —OH).

Starting from 1-(ethoxycarbonyl)piperidin-3,5-dione and butanoic anhydride, the following was prepared: 4-butanoyl-1-(ethoxycarbonyl)piperidin-3,5-dione.

$^1$H-NMR(CDCl$_3$): 0.80–1.79 (m, 8H, aliphatic); 2.91

(t, 2H, —CH$_2$—C=O);

3.90–4.27 (m, 6H, heterocyclic,

—CH$_2$—O—C=O);

17.8 (bs, 1H, —OH).

Starting from 1-(2,4,6-trimethylbenzoyl)piperidin-3,5-dione and butanoic anhydride, the following was prepared: 4-butanoyl-1-(2,4,6-trimethylbenzoyl)piperidin-3,5-dione.

$^1$H-NMR(CDCl$_3$): 0.85 (t, 3H, CH$_3$—); 1.47 (m, 2H, —CH$_2$—); 2.09 (s, 6H, aromatic methyls); 2.17 (s, 3H, aromatic methyl); 3.83

(t, 2H, —CH$_2$—C=O);

3.81 (s, 2H, heterocyclic); 4.50 (s, 2H, heterocyclic); 6.91 (s, 2H, aromatic); 18.1 (bs, 1H, —OH).

Starting from 1-(2,4-dichlorobenzoyl)piperidin-3,5-dione and butanoic anhydride, the following was prepared: 4-butanoyl-1-(2,4-dichlorobenzoyl)piperidin-3,5-dione.

$^1$H-NMR(CD$_3$OD): 0.82 (t, 3H, CH$_3$); 1.46 (m, 2H, —CH$_2$—); 2.99

(t, 2H, —CH$_2$—C=O)

3.79 (s, 2H, heterocyclic); 4.35 (s, 2H, heterocyclic); 7.31–7.44 (m, 3H, aromatic); 18.2 (bs, 1H, —OH).

Starting from 1-(4-chlorobenzoyl)piperidin-3,5-dione and propanoic anhydride, the following was prepared: 4-propanoyl-1-(4-chlorobenzoyl)piperidin-3,5-dione.

$^1$H-NMR(CD$_3$OD): 1.15 (t, 3H, CH$_3$); 2.98

(q, 2H, —CH$_2$—C=O);

4.28 (s, 4H, heterocyclic); 7.36 (s, 4H, aromatic); 18.0 (bs, 1H, —OH).

Starting from 1-(2,6-dichlorobenzoyl)piperidin-3,5-dione and butanoic anhydride, the following was prepared: 4-butanoyl-1-(2,6-dichlorobenzoyl)piperidin-3,5-dione.

$^1$H-NMR(CD$_3$OD): 0.80 (t, 3H, CH$_3$); 1.45 (m, 2H, —CH$_2$—); 3.01

(t, 2H, —CH$_2$—C=O);
|

3.74 (s, 2H, heterocyclic); 4.30 (s, 2H, heterocyclic); 7.31 (s, 3H, aromatic); 18.1 (bs, 1H, —OH).

Starting from 1-(2,6-dichlorobenzoyl)piperidin-3,5-dione and propanoic anhydride, the following was prepared: 4-propanoyl-1-(2,6-dichlorobenzoyl)piperidin-3,5-dione.

$^1$H-NMR(CD$_3$OD): 0.91 (t, 3H, CH$_3$—); 2.99

(q, 2H, —CH$_2$—C=O);
|

3.75 (s, 2H, heterocyclic); 4.32 (s, 2H, heterocyclic); 7.33 (s, 3H, aromatic); 18.1 (bs, 1H, —OH).

Starting from 1-(4-nitrobenzoyl)piperidin-3,5-dione and butanoic anhydride, the following was prepared: 4-butanoyl-1-(nitrobenzoyl)piperidin-3,5-dione.

$^1$H-NMR(DMSO): 0.85 (t, 3H, CH$_3$—); 1.46 (m, 2H, —CH$_2$—); 2.81

(t, 2H, —CH$_2$—C=O);
|

4.25 (s, 4H, heterocyclic); 7.82 (d, 2H, aromatic); 8.44 (d, 2H, aromatic); 18.2 (bs, 1H, —OH);

Starting from 1-(phenyl)piperidin-3,5-dione and butyric anhydride, the following was prepared: 4-butanoyl-1-(phenyl) piperidin-3,5-dione.

$^1$H-NMR(CDCl$_3$): 0.99 (t, 3H, CH$_3$—); 1.65 (m, 2H, —CH$_2$—); 2.91

(t, 2H, —CH$_2$—C=O);
|

3.91 (s, 2H, heterocyclic); 4.12 (s, 2H, heterocyclic); 6.82–7.30 (m, 5H, aromatic); 17.9 (bs, 1H, —OH).

Starting from 1-(benzyl)piperidin-3,5-dione and propanoic anhydride, the following was prepared: 4-propanoyl-1-(benzyl) piperidin-3,5-dione.

$^1$H-NMR(DMSO): 0.93 (t, 3H, CH$_3$—); 2.73 (q, 2H,

—CH$_2$—C=O);
|

3.00 (s, 4H, heterocyclic); 3.51

(s, 2H, —CH$_2$—N$\diagdown^{\diagup}$);

7.29 (s, 5H, aromatic); 18.0 (bs, 1H, —OH).

Starting from 1-(N,N-dimethylaminocarbonyl)piperidin-3,5-dione and butanoic anhydride, the following compound was prepared: 4-butanoyl-1-(N,N-dimethylaminocarbonyl) piperidin-3,5-dione.

$^1$H-NMR(CDCl$_3$): 0.75–1.3 (m, 5H, aliphatic); 2.4–2.8 (m, 2H,

—CH$_2$—C=O);
|

2.8 (s, 6H, —N—(CH$_3$)$_2$); 3.9 (s, 4H, heterocyclic); 18.0 (bs, 1H, OH).

Starting from 1-(N,N-dimethylaminocarbonyl)-2-methyl-piperidin-3,5-dione and butanoic and anhydride, the following compound was prepared: 4-butanoyl-1-(N,N-dimethylaminocarbonyl)-2-methyl-piperidin-3,5-dione.

$^1$H-NMR(CDCl$_3$): 0.8–1.3 (m, 5H, aliphatic); 2.3–2.7 (m, 2H,

—CH$_2$—C=O);
|

2.8 (s, 6H, —N—(CH$_3$)$_2$); 3.7–4.1 (m, 3H, heterocyclic); 18.2 (bs, 1H, OH).

EXAMPLE 4

Determination of the herbicidal activity.

A certain number of pots (diameter over 10 cm and height of 10 cm) containing sandy soil were prepared. In each pot one of the following weeds was sown: Echinochloa Crusgallia, *Avena fatua*, Alopecurus Myosuroides, *Lolium italicum*.

The necessary amount of water was added to each small pot to allow the seeds to germinate well.

The small pots were divided into three groups.

The first group was not treated with any herbicide at all and it was used as a term of comparison (control experiment).

The second group was treated, one day after being sown, with a hydroacetonic dispersion (20% vol./vol.) of the compounds of the invention, in order to evaluate the pre-emergence herbicidal activity.

The third group was treated fifteen days after the seeds had been planted (i.e. when the young plants, in relation to their species, were 10–15 cm tall) with a hydroacetonic dispersion of the compounds of the invention in order to evaluate the post-emergence herbicidal activity.

All the small pots were kept under control in a conditioned environment at temperatures of from 15° C. to 26° C., with a relative humidity of 60%, a photoperiod lasting 12 hours and a luminous intensity of 5000 lux.

All the pots were equally watered every two days, in order to assure a sufficient percentage of humidity permitting the plants to develop well.

Twenty-eight days after the treatment, the activity of the compounds of the invention was evaluated on the grounds of a percentage value scale (0=no herbicidal activity, growth equal to the control experiment; 100=total herbicidal activity, death of plants).

The results obtained using the compounds of the invention, with a dosage of 1 kg/ha of active principle, are reported in Table 1.

TABLE 1

| COMPOUND No | PRE-EMERGENCE | | | | POST-EMERGENCE | | | |
|---|---|---|---|---|---|---|---|---|
| | ECHINOCHLOA CRUSGALLI | AVENA FATUA | ALOPECURUS MYOSUROIDES | LOLIUM ITALICUM | ECHINOCHLOA CRUSGALLI | AVENA FATUA | ALOPECURUS MYOSUROIDES | LOLIUM ITALICUM |
| 1 | 5 | 5 | 20 | 80 | 100 | 100 | 100 | 100 |
| 2 | 0 | 0 | 25 | 10 | 70 | 100 | 100 | 100 |
| 3 | 5 | 0 | 10 | 30 | 20 | 80 | 95 | 40 |
| 4 | 5 | 0 | 10 | 20 | 15 | 50 | 95 | 90 |
| 5 | 10 | 10 | 35 | 50 | 100 | 100 | 100 | 100 |
| 6 | 10 | 15 | 50 | 60 | 100 | 100 | 100 | 100 |
| 7 | 0 | 0 | 20 | 40 | 70 | 0 | 100 | 75 |
| 8 | 10 | 15 | 90 | 95 | 60 | 60 | 100 | 100 |
| 9 | 5 | 0 | 0 | 60 | 20 | 5 | 20 | 35 |
| 10 | 5 | 0 | 5 | 5 | 20 | 20 | 5 | 10 |
| 11 | 0 | 0 | 0 | 0 | 15 | 10 | 5 | 15 |
| 12 | 0 | 0 | 0 | 0 | 10 | 5 | 0 | 0 |
| 13 | 0 | 0 | 0 | 0 | 100 | 5 | 80 | 25 |
| 14 | 5 | 5 | 5 | 10 | 100 | 60 | 40 | 90 |
| 15 | 0 | 0 | 0 | 0 | 30 | 40 | 35 | 35 |
| 16 | 0 | 0 | 5 | 20 | 45 | 60 | 85 | 75 |
| 17 | 0 | 0 | 0 | 0 | 20 | 25 | 10 | 10 |
| 18 | 0 | 0 | 40 | 90 | 20 | 30 | 30 | 30 |
| 19 | 100 | 100 | 100 | 100 | 100 | 100 | 100 | 100 |
| 20 | 100 | 100 | 100 | 100 | 100 | 100 | 100 | 100 |

EXAMPLE 4

Determination of the herbicidal activity. A certain number of pots (dimater over 10 cm and height of 10 cm) containing sandy soil was prepared. In each pot one of the following weeds was sown: Echinochloa Crusgalli, Avena fatua,, Alopecurus Myosuroides, Lolium italicum.

The necessary amount of water was added to each small pot allowing the seeds to germinate well.

The small pots were divided into three groups.

The first group was not treated with any herbicide at all and it was used as a term of comparison (control experiment).

The second group was treated, one day after being sown, with a hydroacetonic dispersion (20% vol./vol.) of the compounds of the invention, in order to evaluate the pre-emergence herbicidal activity.

The third group was treated fifteen days after the seeds had been planted (i.e. when the young plants, in relation to their species, were 10–15 cm tall) with a hydroacetonic dispersion of the compounds of the invention in order to evaluate the post-emergence herbicidal activity.

All the small pots were kept under control in a conditioned environment at temperatures going from 15° C. to 26° C., with a relative humidity=60%, a photoperiod lasting 12 hours and a luminous intensity=5000 lux.

All the pots were equally watered every two days, in order to assure a sufficient percentage of humidity permitting the plants to develop well.

Twenty-eight days after the treatment, the activity of the compounds of the invention was evaluated on the ground of a percentage value scale (0=no herbicidal activity, growth equal to the control experiment; 100=total herbicidal activity, death of plants).

The results obtained using the compounds of the invention, with a dosage of 1 kg/ha of active principle, are reported in Table 1.

What we claim is:

1. A compound represented by the formula:

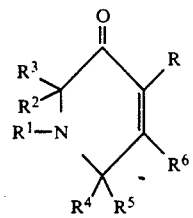

wherein R is —CO—R$^7$,

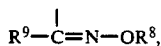

or —NH—COR$^{10}$; wherein R$^7$ and R$^9$, which are the same or different, are C$_1$-C$_6$ alkyl, cycloalkyl, naphthyl, or phenyl which is unsubstituted or substituted by halogen, —CN, —NO$_2$, —CH$_3$, —SOCH$_3$, —OCH$_3$, or —CF$_3$; R$^8$ is C$_1$-C$_6$ alkyl which is unsubstituted or substituted by 1-4 C$_2$-C$_6$ alkynyl which is unsubstituted or substituted by 1-4 halogen, C$_2$-C$_6$ alkenyl which is unsubstituted or substituted by 1-4 halogens, C$_3$-C$_6$ alkynyl, C$_3$-C$_7$ cycloalkyl, C$_7$-C$_{20}$ aralkyl or phenyl which is unsubstituted or substituted by halogen, —CN, —NO$_2$, —CH$_3$, or —CF$_3$; R$^{10}$ is phenyl which is unsubstituted or substituted by halogen, —CN, —NO$_2$, —CH$_3$, —OCH$_3$ or —CF$_3$; R$^2$, R$^3$, R$^4$ and R$^5$, which are the same or different, are hydrogen, or C$_1$-C$_3$ alkyl which is unsubstituted or substituted by 1-4 halogen; R$^6$ is —OR$^{11}$,

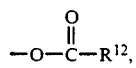

—S(O)$_m$—R$^{13}$, —NR$^{14}$R$^{15}$, halogen,

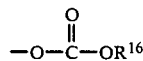

or —O—S(O)$_q$—R$^{17}$; wherein R$^{11}$ is hydrogen, alkali metal or alkaline earth metal; R$^{12}$ and R$^{13}$, which are the same or different, are C$_1$-C$_6$ alkyl which is unsubstituted or substituted by 1-4 halogen; C$_3$-C$_6$ cycloalkyl; C$_7$-C$_{20}$ aralkyl, or phenyl which is unsubstituted or substituted by halogen, —CN, —NO$_2$, —CH$_3$, —OCH$_3$, —CF$_3$ or dialkylamino; m and q, which are the same or different, are 0, 1 or 2; R$^{14}$ and R$^{15}$, which are the same or different, are hydrogen, C$_1$-C$_6$ alkyl, C$_1$-C$_6$ alkoxy;

R$^{16}$ is C$_1$-C$_6$ alkyl, C$_2$-C$_6$ alkenyl, C$_7$-C$_{20}$ aralkyl or phenyl which is unsubstituted or substituted by halogen, —NO$_2$, —CN, —CF$_3$, —CH$_3$ or —OCH$_3$;

R$^{17}$ is C$_1$-C$_6$ alkyl or phenyl which is unsubstituted or substituted by halogen, —NO$_2$, —CN, —CF$_3$, or —OCH$_3$;

R$^1$ is phenyl which is unsubstituted or substituted by halogen, —NO$_2$, —CN, —CF$_3$, C$_7$-C$_{20}$ alkyl; C$_7$-C$_{20}$ aralkyl; C$_3$-C$_7$ cycloalkyl or —OR$^{18}$; wherein R$^{18}$ is C$_1$-C$_{10}$ alkyl, phenyl which is unsubstituted or substituted by halogen, —NO$_2$ or —CN, C$_7$-C$_{20}$ aralkyl which is unsubstituted or substituted by halogen;

wherein X is selected from the group consisting of O and S, and Y is phenyl which is unsubstituted or substituted by halogen, —NO$_2$, —CN, —CF$_3$, aryloxy or arylamino; C$_3$-C$_6$ cycloalkyl; C$_1$-C$_8$ alkyl unsubstituted or substituted by 1-11 halogen; —R$^{19}$—X$^1$—R$^{20}$; —X—R$^{21}$; —R$^{22}$—X$^1$—R$^{23}$—X$^2$—R$^{24}$; —NR$^{25}$R$^{26}$; wherein R$^{19}$ is C$_1$-C$_{16}$ alkyl or aralkyl; R$^{20}$ is C$_1$-C$_{16}$ alkyl which is unsubstituted or substituted by 1-6 halogen, C$_3$-C$_6$ alkenyl, C$_3$-C$_6$ alkynyl, C$_3$-C$_7$ cycloalkyl, phenyl, or C$_7$-C$_{13}$ phenylalkyl; R$^{21}$ is C$_1$-C$_{16}$ alkyl unsubstituted or substituted by 1-6 halogen, C$_3$-C$_8$ alkenyl, C$_3$-C$_6$ alkynyl, C$_3$-C$_7$ cycloalkyl, aralkyl, phenyl, —R$^{19}$—X$^1$—R$^{20}$; R$^{22}$, R$^{23}$ and R$^{24}$, same or different are C$_1$-C$_{16}$ alkyl; R$^{25}$ and R$^{26}$, same or different, are hydrogen, C$_1$-C$_{16}$ alkyl, C$_1$-C$_6$ alkoxy, phenyl which is unsubstituted or substituted by halogen, —NO$_2$, —CN, CF$_3$, —OCF$_3$, —SO$_2$—phenyl, or —CO—phenyl; and X$^1$ and X$^2$, are the same or different, and are selected from the group consisting of O, S, So and SO$_2$ aryl is defined as phenyl or naphthyl.

2. A compound according to claim 1, having the formula

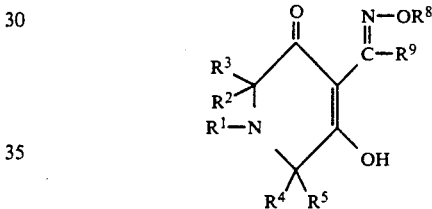

and dione tautomers thereof wherein R$^1$, R$^2$, R$^3$, R$^4$, R$^5$, R$^8$ and R$^9$ have the same meaning as in claim 1.

3. A compound according to claim 2, wherein: R$^8$ is C$_1$-C$_6$ alkyl, or C$_2$-C$_6$ chloroalkenyl; R$^9$ is C$_1$-C$_6$ alkyl; R$^2$, R$^3$, R$^4$, and R$^5$ are hydrogen; R$^1$ represents phenyl, C$_7$-C$_{20}$ phenylalkyl, or

where X is selected from the group consisting of O and S, and Y represents: C$_1$-C$_8$ alkyl, C$_3$-C$_6$ cycloalkyl, phenyl unsubstituted or substituted by halogen or NO$_2$, or Y represents —R$^{19}$—X—R$^{20}$, wherein R$^{19}$ is C$_1$-C$_{16}$ alkyl and R$^{20}$ is C$_1$-C$_6$ alkyl.

4. The compound according to claim 3 which is 1-(2-ethylthiopropanoyl)-4-[1-(ethoximino)butyl]piperidin-3, 5-dione.

5. The compound according to claim 3 which is 4-[1-(ethoximino)butyl]-1-(3-methylbutanoyl)piperidin-3, 5-dione.

6. The compound according to claim 3 which is 4-[1-(3-chloroallyloximino)butyl]-1-(3-methylbutanoyl)-piperidin-3, 5-dione.

7. The compound according to claim 3 which is 4-[1-(ethoximino)butyl]-1-(n-pentanoyl)piperidin-3, 5-dione.

8. The compound according to claim 3 which is cis-4-[1-(3-chloroallyloximino)butyl]-1-(2-ethylthiopropanoyl) piperidin-3, 5-dione.

9. The compound according to claim 3 which is trans-4-[1-(3-chloroalllyloximino)butyl]-1-(2-ethylthiopropanoyl)piperidin-3, 5-dione.

10. The compound according to claim 3 which is 1-(cyclohexanoyl)-4-[1-(ethoximino)butyl]piperidin-3, 5-dione.

11. The compound according to claim 3 which is 1-(ethoxycarbonyl)-4-[1-(ethoximino)butyl]piperidin-3, 5-dione.

12. The compound according to claim 3 which is 4-[1-(ethoximino)butyl]-1-(2,4,6-trimethylbenzoyl)-piperidin-3, 5-dione.

13. The compound according to claim 3 which is 1-(2,4-dichlorobenzoyl)-4-[1-(ethoximino)butyl]piperidin-3, 5-dione.

14. The compound according to claim 3 which is cis-4-[1-(3-chloroalllyloximino)butyl]-1-(2,4-dichlorobenzoyl)piperidin-3, 5-dione.

15. The compound according to claim 3 which is trans-4-[1-(3-chloroalllyloximino)butyl]-1-(2,4-dichlorobenzoyl)piperidin-3, 5-dione.

16. The compound according to claim 3 which is 1-(4-chlorobenzoyl)-4-[1-(ethoximino)propyl]piperidin-3, 5-dione.

17. The compound according to claim 3 which is 1-(2,6-dichlorobenzoyl)-4-[1-(ethoximino)butyl]piperidin-3, 5-dione.

18. The compound according to claim 3 which is 1-(2,6-dichlorobenzoyl)-4-[1-(ethoximino)propyl]-piperidin-3, 5-dione.

19. The compound according to claim 3 which is 4-[1-(ethoximino)butyl]-1-(4-nitrobenzoyl)piperidin-3, 5-dione.

20. The compound according to claim 3 which is 4-[1-(ethoximino)butyl]-1-(phenyl)piperidin-3, 5-dione.

21. The compound according to claim 3 which is 1-(benzyl)-4-[1-(ethoximino)propyl]piperidin-3, 5-dione.

22. A method for controlling weeds which grow among agricultural crops comprising distributing a herbicidally effective amount of a compound of claim 1, either along or with an inert carrier, on soil or weeds.

23. A herbicidal composition comprising a herbicidally, effective amount of a compound of claim 1 and an inert carrier.

* * * * *